United States Patent
Frey, II

(10) Patent No.: US 10,092,630 B2
(45) Date of Patent: Oct. 9, 2018

(54) METHODS OF TREATING ANOREXIA NERVOSA BY INTRANASAL ADMINISTRATION OF INSULIN

(71) Applicant: HealthPartners Institute, Bloomington, MN (US)

(72) Inventor: William H. Frey, II, St. Paul, MN (US)

(73) Assignee: HealthPartners Institute, Bloomington, MN (US)

( * ) Notice: Subject to any disclaimer, the term of this patent is extended or adjusted under 35 U.S.C. 154(b) by 70 days.

(21) Appl. No.: 15/340,160

(22) Filed: Nov. 1, 2016

(65) Prior Publication Data

US 2017/0128543 A1     May 11, 2017

Related U.S. Application Data

(60) Provisional application No. 62/251,991, filed on Nov. 6, 2015.

(51) Int. Cl.
| | | |
|---|---|---|
| *A61K 38/28* | (2006.01) | |
| *A61K 9/00* | (2006.01) | |
| *A61K 45/06* | (2006.01) | |

(52) U.S. Cl.
CPC ............ *A61K 38/28* (2013.01); *A61K 9/0043* (2013.01); *A61K 45/06* (2013.01)

(58) Field of Classification Search
None
See application file for complete search history.

(56) References Cited

U.S. PATENT DOCUMENTS

2014/0255384 A1    9/2014 Frey, II

OTHER PUBLICATIONS

Harrington et al. "Initial Evaluation, Diagnosis, and Treatment of Anorexia Nervosa and Bulimia Nervosa" American Family Physician, vol. 91, Jan. 1, 2015, pp. 46-53 (Year: 2015).*
Jauch-Chara et al. "Intranasal Insulin Suppresses Food Intake via Enhancement of Brain Energy Levels in Humans" Diabetes 2012; 61(9):2261-2268 (doi: 10.2337/db12-0025) p. 2265, col. 2, para 2.
Hallschmid et al., "Intranasal Insulin Reduces Body Fat in Men but not in Women" Diabetes 2004; 53(11):3024-3029 (doi: 10.2337/diabetes.53.11.3024) Figure 1.
Benedict et al., "Differential sensitivity of men and women to anorexigenic and memory-improving effects of intranasal insulin" J Clin endocrinol Metab. 2008; 93(4):1339-1344 (doi: 10.1210/jc.2007-2606) p. 1341, col. 1, para 4.
International Search Report and Written Opinion for PCT Application No. PCT/US2016/060297, filed Nov. 3, 2016, dated Jan. 10, 2017.
International Preliminary Report on Patentability, dated May 8, 2018, for PCT Application No. PCZT/US2016/060297, filed Nov. 3, 2016.

* cited by examiner

*Primary Examiner* — Christina Bradley
(74) *Attorney, Agent, or Firm* — Barnes & Thornburg LLP; Jeffrey R. Stone

(57) ABSTRACT

The present system is directed in several embodiments to a method of administration of a therapeutic composition for treatment of Anorexia Nervosa, safely and without significantly affecting the blood glucose or blood insulin levels of the patient. The method includes administering one or more therapeutic compositions comprising an effective amount of insulin directly to the subject patient's CNS, with no to minimal systemic exposure. Preferably, this method comprises administration of an effective amount of insulin to the upper third of a patient's nasal cavity, thereby bypassing the patient's blood-brain barrier and delivering the therapeutic composition directly to the patient's central nervous system.

19 Claims, No Drawings

METHODS OF TREATING ANOREXIA NERVOSA BY INTRANASAL ADMINISTRATION OF INSULIN

CROSS-REFERENCE TO RELATED APPLICATIONS

This application claims priority to provisional application 62/251,991, filed Nov. 6, 2016 and entitled TREATMENT OF ANOREXIA NERVOSA BY INTRANASAL INSULIN, the entire contents of which are hereby incorporated by reference.

FEDERAL FUNDING

None

BACKGROUND OF THE INVENTION

Field of the Invention

The present invention is directed to methods of treating patients diagnosed with Anorexia Nervosa. More particularly, the present disclosure is directed to a method of treating patients with Anorexia Nervosa by administration of an effective amount of insulin to the upper third of the patient's nasal cavity.

Description of the Related Art

Delivery of the agent and/or composition to the upper one third of the patient's nasal cavity is a means of bypassing the BBB to administer therapeutic compounds and/or agents directly to the CNS. Evidence exists that intranasal treatment with certain therapeutic agent(s) improves, i.e., prevents and/or treats, a variety of neurological and psychiatric disorders, e.g., stroke, in animals. This basic methodology is discussed and described in U.S. Pat. No. 5,624,898 to Frey II entitled Method for Administering Neurologic Agents to the Brain, as well as in U.S. Pat. No. 6,313,093 to Frey II, the entire contents of each of which are hereby incorporated by reference. This administration technique is a vast improvement over systemic administration methods such as intravenous and oral administration of drugs which generally cannot cross the BBB to reach their targets within the CNS. In addition, Frey's intranasal method is a significant improvement over the general inhalation methods which target the lower two-thirds of the patient's nasal cavity. Both the systemic and general intranasal method targeting the lower two-thirds of the nasal cavity result in a very large, unwanted and potentially dangerous systemic exposure to the administered drug or therapeutic agent(s). The present invention addresses, inter alia, this general intranasal problem as well as ensures that the patient's non-CNS, systemic disease and/or condition is protected from exposure to the therapeutic agent administered to the upper third of the nasal cavity, and potential harm therefrom.

General inhalation methods to the lower two-thirds of the nasal cavity delivered by, e.g., nasal spray bottles, on the other hand, result in a large amount of systemic absorption and exposure, with a very small amount of the administered compound, i.e., less than 5%, making the tortuous journey around the turbinates to the upper third of the nasal cavity and still less compound than that very small amount further bypassing the BBB to actually reach the CNS.

Delivery and administration to the upper third of the nasal cavity, is very effective in administering the subject compounds or agents to the desired target, i.e., the CNS, without significant systemic exposure, though some systemic exposure does occur as is further discussed below.

Unwanted systemic exposure of therapeutics used to treat CNS diseases create several serious problems. The systemic metabolism greatly reduces the bioavailability of any agent and/or compound exposed to the non-CNS system. This reduction of bioavailability is increased by unwanted plasma protein binding of the agent and/or compound. As a result, only a small amount of the active therapeutic agent and/or compound actually reaches the CNS. Because of these, inter alia, issues, the actual dose that must be administered in order to achieve a therapeutic dose in the targeted CNS is far larger than the therapeutic dosing. As a consequence, a relatively large concentration of the agent(s) and/or compounds(s) is in the system and will affect non-target systemic organs and systems. This can create unwanted and often dangerous side effects on these non-target organs and systems, particularly in the specific case of patient's having a systemic, non-CNS disorder or condition that contraindicates the systemic use or exposure of the therapeutic agent(s) needed to treat a CNS-related disorder or condition.

We have addressed the efficiency needs in patent application Ser. No. 12/134,385 to Frey II, et al., entitled "Pharmaceutical Compositions and Methods for Enhancing Targeting of Therapeutic Compounds to the Central Nervous System, the entire contents of which are hereby incorporated by reference, and wherein a vasoconstrictor is administered to the patient's nasal cavity either just prior to, or in combination with, administration of at least one therapeutic agent and/or pharmaceutical composition(s) comprising a therapeutic compound(s) and/or agent(s). The efficiency of the direct administration of the pharmaceutical compound to the CNS, with concomitant reduction of systemic exposure of the pharmaceutical compound is remarkable.

Moreover, we provide disclosure of the following patents and applications, each of which are commonly assigned with the present application and incorporated herein in their entirety for disclosure of, inter alia, the various diseases, conditions or disorders of the CNS relating herein to the first disease or condition of the present invention, as well as various compounds and/or therapeutic agents for treating same by application to the upper third of the nasal cavity, thereby bypassing the blood-brain barrier, with subsequent direct delivery of an effective amount of the compounds and/or agents to the CNS:

U.S. Pat. No. 7,972,595 Methods and compositions for protecting and treating at least one muscarinic receptor from dysfunction not resulting from oxidative stress, toxic actions of metals or infectious agents by administering a pyrophosphate analog;

U.S. Pat. No. 7,786,166 Methods and compositions for protecting and treating muscarinic receptors through administration of at least one protective agent;

U.S. Pat. No. 7,776,312 Method of treating Alzheimer's disease comprising administering deferoxamine (DFO) to the upper one-third of the nasal cavity;

U.S. Pat. No. 7,618,615 Methods for providing neuroprotection for the animal central nervous system against neurodegeneration caused by ischemia;

U.S. Pat. No. 7,084,126 Methods and compositions for enhancing cellular function through protection of tissue components;

U.S. Pat. No. 6,313,093 Method for Administering Insulin to the Brain;

US Pat Application 20100061959 Methods for Providing Neuroprotecton for the Animal Central Nervous System Against the Effects of Ischemia, Neurodegeneration, Trauma, and Metal Poisoning;

US Patent Application 20080305077 Pharmaceutical Compositions and Method for Enhancing Targeting of Therapeutic Compounds to the Central Nervous System;

US Patent Application 20110311654 Methods and Pharmaceutical Compositions for Treating the Animal Central Nervous System for Psychiatric Disorders;

US Patent Application 20110236365 Method for Protecting and Treating at Least One Muscarinic Receptor From Dysfunction Resulting From Free Radical Damage.

The present invention provides solutions for, inter alia, these problems.

SUMMARY OF THE INVENTION

The present system is directed in one embodiment to a method of administration of a therapeutic compound and/or composition for patients with Anorexia Nervosa. The method includes administering one or more therapeutic compositions comprising an effective amount of insulin directly to the subject patient's CNS, with none, or minimal, systemic exposure. Preferably, this method comprises administration to the upper third of a patient's nasal cavity, thereby bypassing the patient's blood-brain barrier and delivering the therapeutic compound and/or composition directly to the patient's central nervous system.

DETAILED DESCRIPTION OF THE INVENTION

Definitions

As used herein, "central nervous system" (CNS) refers to the brain and spinal cord and associated cells and tissues.

As used herein, "systemic administration" refers to administration of a medication, pharmaceutical and the like by the following non-limited means: oral, intravenous, intra-arterial, intramuscular, epidermal, transdermal, subcutaneous, topic, sublingual as well as general inhalation, i.e., administration to the lower two-thirds of the patient's nasal cavity. In each of these cases, the administered drug will migrate through the patient's circulatory system and, in order to reach the patient's CNS would be required to cross the patient's blood-brain barrier.

In the context of the present invention, the terms "treat" and "therapy" and the like refer to alleviate, slow the progression, prophylaxis, attenuation or cure of existing disease or condition that has or is causing cell death in the CNS.

"Prevent", as used herein, refers to putting off, delaying, slowing, inhibiting, or otherwise stopping, reducing or ameliorating the onset of such diseases or disorders. It is preferred that a large enough quantity of the therapeutic agent(s) and/or compound(s) be applied in non-toxic levels in order to provide an effective level of activity against the disease. The method of the present invention may be used with any animal, such as a mammal or a bird (avian), more preferably a mammal. Poultry are a preferred bird. Exemplary mammals include, but are not limited to rats, mice, cats, dogs, horses, cows, sheep, pigs, and more preferably humans.

An "effective amount" of therapeutic agent(s), i.e., insulin, and/or component(s) of the pharmaceutical composition of the present invention comprising therapeutic agent(s) is an amount sufficient to treat, reduce and/or ameliorate the symptoms, neuronal damage and/or underlying causes of Anorexia Nervosa. In some instances, an "effective amount" may be sufficient to eliminate the symptoms of Anorexia Nervosa and overcome the disease itself. Preferably, at least an effective amount of the at least one therapeutic agent, i.e., insulin, and/or component(s) of the pharmaceutical composition yields a tissue concentration in the range of about $10^{-13}$ molar to about $10^{-9}$ molar, but the concentrations may be greater provided that toxicity is avoided. Generally, at least an effective amount of insulin or pharmaceutical composition(s) thereof is administered in order to ensure that an effective amount of insulin is delivered to the target CNS for treating Anorexia Nervosa.

The concentration range of insulin delivered to the upper third of the patient's nasal cavity may be preferably in the range of $10^{-10}$ molar to about $10^{-6}$ molar in order to yield the preferable tissue concentration range of about $10^{-13}$ molar to about $10^{-9}$ molar, though as discussed above, concentrations in the tissue may be higher so long as toxicity is avoided.

For illustrative purposes only, exemplary treatment regimens relating generally to the therapeutic agent, i.e., insulin, and/or pharmaceutical compounds disclosed herein, including dosage ranges, volumes and frequency are provided below:

Efficacious dosage range for the at least one therapeutic agent, i.e., insulin, delivery-enhancement agents, vasoconstrictors and/or antibiotics comprises $1 \times 10^{-7}$ to 0.1 mg/kg. A more preferred dosage range may be $1 \times 10^{-4}$ to 0.1 mg/kg. The most preferred dosage range may be 0.01 to 1 mg/kg. The dosage volume (applicable to nasal sprays or drops) range may be 0.015 ml-1.0 ml.

The preferred dosage volume (applicable to nasal sprays or drops) range may be 0.03 ml-0.6 ml.

The brain concentrations that are likely to be achieved with the dosage ranges provided above are for each of the therapeutic agents described above, including insulin, for a single dose: $1 \times 10^{-13}$ to $1 \times 10^{-9}$ M. Over the course of a multi-dose treatment plan, the maximum brain concentration may be as high as 50 µM for delivery-enhancement agents and antibiotics.

The present disclosure is generally directed to administering insulin intranasally to patients for treatment of Anorexia Nervosa.

Generally, the method of the present invention comprises treating Anorexia Nervosa with the direct non-invasive delivery of a therapeutic, i.e., effective, amount or dose of insulin, or a pharmaceutical composition thereof, to the CNS. This may be accomplished by administration of at least an effective or therapeutic amount of insulin, or pharmaceutical composition thereof, to the upper one-third of the patient's nasal cavity, thereby delivering the effective or therapeutic amount or dose directly to the patient's CNS, with minimal systemic exposure.

In some embodiments, the therapeutic agent—insulin—may be combined with a vasoconstrictor to be administered intranasally to limit systemic exposure. The vasoconstrictor may be administered to the nasal cavity prior to administration of the therapeutic compound to the upper third, or alternatively to the lower two-thirds, of the nasal cavity or, still more alternatively, the vasoconstrictor and therapeutic compound may be administered concurrently, either to the upper one-third or the lower two-thirds of the patient's nasal cavity. Thus, the present invention allows for a safe and efficacious treatment of a patient's Anorexia Nervosa where systemic administration or exposure is contraindicated.

Underweight patients with Anorexia Nervosa have a global and regional glucose cerebral hypometabolism which is more important in the frontal and parietal cortices. (Delvenne et al. (1995) Biol. Psychiatry 37:161-169). Hypercortisolemnnia also occurs in Anorexia Nervosa and is associated with comorbid mood disorders, neurocognitive deficits, hippocampal atrophy, amenorrhea, myopathy and bone loss in Anorexia Nervosa. (Lawson and Klibanski (2008) Nature Clinical Practice 4(7):407-414). Intranasal insulin treatment has been shown to reduce the increased cortisol response to stress in men and to maintain the uptake and metabolism of glucose in the brain of patients with Alzheimer's disease. (Craft et al. (2012) Arch Neurol. 69(1):29-38). Further, patients with Anorexia Nervosa have been reported to have increased insulin sensitivity. (Dostalova et al. (2007) Physiol Res 56:587-594).

However, treatment of Anorexia Nervosa is decidedly non-obvious as it has been reported that "intranasal insulin suppresses food intake via enhancement of brain energy levels in humans" when normal healthy young men were treated in a clinical trial. (Jauch-Chara et al. (2012) Diabetes 61:2261-2268). Further, treatment of Anorexia Nervosa with intranasal insulin is also not obvious because it has been reported that "high baseline cortisol level predicts increases in body fat." (Misra et al. (2006) Pediatr Res 59:598-603). Both of these reports teach against the use of intranasal insulin for treating Anorexia Nervosa.

In addition, patients with Anorexia Nervosa typically have blood (systemic) insulin and glucose levels that are within the normal range, unless the disease is severe and advanced. Systemic administration in these patients will, as discussed herein, result in loss of the administered insulin to non-target systemic insulin receptors, organs and tissues, presenting an increased risk of insulin shock or catastrophic hypoglycemia as blood insulin levels rise and blood glucose levels fall. A relatively small portion of the systemically administered insulin will cross the blood-brain barrier to reach the patient's CNS tissues, but in order to achieve an "effective dose" the insulin dosing will require a massive and dangerous overdosing to compensate for the systemic loss, highlighting the risk of insulin shock or catastrophic hypoglycemia in patients with Anorexia Nervosa. As a result, it would not be obvious to treat patients with Anorexia Nervosa with insulin.

However, even if the particular patient with Anorexia Nervosa has abnormal glucose levels, treatment of insulin with the presently claimed administration to the upper third of the patient's nasal cavity with direct delivery to the CNS will have very little effect on the patient's blood insulin and glucose levels. This is because, once the delivered insulin dosing is located within the patient's CNS, very little of the insulin within the CNS will be transported out of the CNS to the patient's bloodstream; the transport of insulin into the CNS is far faster and much more efficient than transport of insulin out of the CNS. In this way, the dangers of systemic exposure of insulin in patients with Anorexia Nervosa is avoided in two respects: first, minimization of systemic exposure by directly delivering an effective amount of insulin directly to the brain; and second, once the delivered effective amount of insulin is within the brain, the vast majority of the insulin delivered directly to the brain/CNS remains within the brain/CNS. Consequently, even patients with abnormal glucose levels may be safely treated using the present invention.

There are a variety of types of insulin available that may be used in accordance with the present disclosure, including insulins for which zinc is included for stabilization and others which do not include zinc. Because zinc may be detrimental to the olfactory system, insulins that do not contain zinc may be preferable in some cases. Formulations of insulin that either contain no preservatives (which could be prepared for unit dosing) or a safe preservative such as pyrophosphate are preferred. In some embodiments the insulin formulation may not include any phenol or cresol preservatives.

It is preferred that the neurologic agent—insulin—promote nerve cell growth and survival or augment the activity of functioning cells. The neurologic agent may be administered intranasally as a powder, spray, gel, ointment, infusion, injection, or drops, for example. The insulin may be administered in an effective dose. The intranasal composition may be dispensed as a powder or liquid nasal spray, nose drops, a gel or ointment, through a tube or catheter, by syringe, by packtail, by pledget, or by submucosal infusion. Any suitable nasal spray device may be used with embodiments of the present disclosure.

In some embodiments, the composition may include the neurologic therapeutic agent (insulin) as well as a vasoconstrictor that may generally enhance the intranasal therapeutic compound targeting the CNS, as is further described in U.S. patent application Ser. No. 12/134,385, entitled, "Pharmaceutical Compositions and Methods for Enhancing Targeting of Therapeutic Compounds to the Central Nervous System," filed on Jun. 6, 2008, which is hereby incorporated herein in its entirety. As provided in the aforementioned application, constriction of blood vessels resulting from action of the vasoconstrictor in the nasal cavity facilitates transport of the therapeutic compound(s) or agent(s) into the brain along olfactory and trigeminal neural pathways, perivascular pathways, or lymphatic pathways. Thus, intranasal delivery of a therapeutic compound(s) or agent(s) in combination with an agent that constricts blood vessels (i.e. a vasoconstrictor) within or in the proximity of the mucosa of the nasal cavity enhances intranasal drug targeting to, inter alia, the CNS by reducing absorption into the blood, increasing CNS concentrations (as well as other targeted locations), or both.

In one embodiment, the pharmaceutical composition may be comprised of a combination of at least one therapeutic compound comprising insulin and at least one vasoconstrictor. In another embodiment, at least one vasoconstrictor may be applied intranasally or otherwise, i.e., intravenously, topically as a pretreatment or concurrently with administration of at least one therapeutic compound.

Inclusion of vasoconstrictors in intranasal formulations that include insulin for prevention and/or treatment of Anorexia Nervosa may include, but are not limited to providing the following advantages: reducing absorption into the blood, which is desirable for drugs with adverse side effects in the blood or in peripheral tissues; reducing systemic drug exposure, which is important for drugs that are rapidly eliminated in drug metabolizing organs or for drugs that are extensively bound to plasma proteins; targeting drugs to the olfactory epithelium for CNS delivery of drugs; reducing clearance of the drug into the blood from the nasal cavity, which increases the residence time and contact with the nasal epithelium; targeting drugs to the olfactory epithelium, olfactory bulbs and/or anterior olfactory nucleus to have therapeutic potential for the treatment of Anorexia Nervosa; targeting high potency drugs to the frontal cortex to reach brain targets involved in cognition disorders, motor dysfunction in Anorexia Nervosa; and targeting the hippocampus for treatment of learning and memory disorders associated with Anorexia Nervosa.

Exemplary vasoconstrictors in the various embodiments of the present invention may comprise, without limitation, PHE and/or THZ. Additional vasoconstrictors will be well known to the skilled artisan and may include, again without limitation, methoxamine, phenylephrine, ephedrine, norepinephrine, oxymatazoline, tetrahydrozoline, xylometazoline, clonidine, guanabenz, guanfacine, α-methyldopa, and/or arginine vasopressin.

An at least an effective amount, as herein defined, of the therapeutic compound, i.e., insulin, and/or vasoconstrictor to be administered pursuant to embodiments of the invention is the most preferred method of expression of dosage. Such effective amount is dependent upon many factors, including but not limited to, the type of disease or condition and its severity, i.e., the severity of the patient's Anorexia Nervosa, the patient's general health, size, age, and the nature of the treatment, i.e. short-term or chronic treatment.

Generally, the treatment may be given in a single dose or multiple administrations, i.e., once, twice, three or more times daily over a period of time. In some cases, one or more doses daily may be given over an extended period of time, including, months or years.

The method of the invention administers an at least an effective amount of the insulin, or pharmaceutical compound thereof, to the upper third of the nasal cavity of a mammal. It is preferred that the at least an effective amount of insulin be administered to the olfactory area in the upper third of the nasal cavity and particularly to the olfactory epithelium in order to promote transport of the agent into the peripheral olfactory neurons rather than the capillaries within the respiratory epithelium. In some embodiments it may be preferable to transport insulin to the brain by means of the nervous system instead of the circulatory system so that therapeutic agents that are unable to cross the blood-brain barrier from the bloodstream into the brain may be delivered to damaged neurons in the brain.

Transportation Pathway to Bypass Blood-Brain Barrier
The Olfactory Nerve

Various methods of the present invention include administration of at least an effective amount of insulin and/or pharmaceutical composition(s) thereof to tissue innervated by the olfactory nerve and that is located in the upper third of the nasal cavity. The at least an effective amount of insulin and/or pharmaceutical composition(s) thereof can be delivered to the olfactory area via application to the upper third of the nasal cavity.

Fibers of the olfactory nerve are unmyelinated axons of olfactory receptor cells that are located in the upper one-third of the nasal mucosa. The olfactory receptor cells are bipolar neurons with swellings covered by hair-like cilia that project into the nasal cavity. At the other end, axons from these cells collect into aggregates and enter the cranial cavity at the roof of the nose. Surrounded by a thin tube of pia, the olfactory nerves cross the subarachnoid space containing CSF and enter the inferior aspects of the olfactory bulbs. Once the therapeutic agent(s) and/or pharmaceutical composition(s) of the present invention is applied to the upper third of nasal cavity, the therapeutic agent(s) and/or pharmaceutical composition(s) of the present invention can undergo transport through the nasal mucosa and into the olfactory bulb and other areas of the CNS, such as the anterior olfactory nucleus, frontal cortex, hippocampal formation, amygdaloid nuclei, nucleus basalis of Meynert, hypothalamus, midbrain, cerebellum, cervical spinal cord and the like.

Neuronal Transport

Embodiments of the present method includes administration of an at least an effective amount of insulin and/or pharmaceutical composition(s) thereof of the present invention to the subject by application to the upper third of the mammalian subject's nasal cavity. Application of the at least an effective amount of insulin and/or pharmaceutical composition(s) thereof of the present invention in this manner ensures that an effective amount of insulin and/or pharmaceutical composition(s) are transported to the CNS, brain, and/or spinal cord along a neural pathway, with reduced systemic loss and, therefore, minimized systemic exposure. A neural pathway includes transport within or along a neuron, through or by way of lymphatics running with a neuron, through or by way of a perivascular space of a blood vessel running with a neuron or neural pathway, through or by way of an adventitia of a blood vessel running with a neuron or neural pathway, or through an hemangiolymphatic system.

The present invention comprises transportation of the administered insulin and/or pharmaceutical composition(s) thereof by way of a neural pathway, rather than through the circulatory system, so that agent(s) and/or compound(s) that are unable to, or only poorly, cross the blood-brain barrier from the bloodstream into the brain can be delivered to the lymphatic system, CNS, brain, and/or spinal cord. The therapeutic agent(s) and/or pharmaceutical composition(s) of the present invention, once past the blood-brain barrier and in the CNS, can then be delivered to various areas of the brain or spinal cord through lymphatic channels, through a perivascular space, or transport through or along neurons.

Use of a neural pathway to transport a therapeutic agent(s) and/or pharmaceutical composition(s) to the brain, spinal cord, or other components of the central nervous system obviates the obstacle presented by the blood-brain barrier so that medications, i.e., therapeutic agent(s) and/or pharmaceutical compositions of the present invention, that cannot normally cross that barrier, can be delivered directly to the CNS, e.g., the brain and spinal cord. In addition, the present invention can provide for delivery of a more concentrated level of the therapeutic agent(s) and/or pharmaceutical composition(s) of the present invention to the CNS since the therapeutic agent(s) and/or pharmaceutical composition(s) of the present invention do not become diluted in fluids present in the bloodstream. As such, the invention provides an improved method for delivering an effective amount or therapeutic dose of the administered insulin and/or pharmaceutical composition(s) thereof directly to the target CNS including the brain and/or spinal cord.

The Olfactory Neural Pathway

One embodiment of the present method includes delivery of the effective amount of insulin to the subject's CNS for prevention and treatment of Anorexia Nervosa in a manner such that the at least an effective amount of insulin administered to the upper third of the nasal cavity is transported into the CNS, e.g., the brain, and/or spinal cord along an olfactory neural pathway. Typically, such an embodiment includes administering the at least an effective amount of insulin and/or other compound(s) to tissue innervated by the olfactory nerve and inside the nasal cavity. The olfactory neural pathway innervates primarily the olfactory epithelium in the upper third of the nasal cavity, as described above. Application of the at least an effective amount of insulin to a tissue innervated by the olfactory nerve can deliver an effective amount of insulin and/or compound(s) to damaged neurons or cells of the CNS, including but not limited to the brain, and/or spinal cord. Olfactory neurons innervate this tissue and can provide a direct connection to the CNS, brain, and/or spinal cord due, it is believed, to their role in olfaction.

Delivery through the olfactory neural pathway can employ lymphatics that travel with the olfactory nerve to the various brain areas and from there into dural lymphatics associated with portions of the CNS, such as the spinal cord.

Transport along the olfactory nerve can also deliver an effective amount of insulin and/or compound(s) to an olfactory bulb. A perivascular pathway and/or a hemangiolymphatic pathway, such as lymphatic channels running within the adventitia of cerebral blood vessels, can provide an additional mechanism for transport of an effective amount of insulin, e.g., to the brain and spinal cord from tissue innervated by the olfactory nerve.

At least an effective amount of insulin, and/or pharmaceutical compositions thereof may be administered to the olfactory nerve, for example, through the olfactory epithelium located at the upper one-third of the nasal cavity. Such administration can employ extracellular or intracellular (e.g., transneuronal) anterograde and retrograde transport of the agent(s) and/or compound(s) entering through the olfactory nerves to the brain and its meninges, to the brain stem, or to the spinal cord. Once the at least an effective amount, i.e., therapeutic dose, of the insulin and/or pharmaceutical composition thereof is dispensed into or onto tissue innervated by the olfactory nerve, the administered insulin and/or pharmaceutical composition and/or components thereof may be transported through the tissue and travel along olfactory neurons into areas of the CNS including but not limited to the brain stem, cerebellum, spinal cord, cerebrospinal fluid, olfactory bulb, and cortical and subcortical structures. Thus, an effective amount of insulin and/or pharmaceutical composition thereof, is delivered to the target CNS for prevention and/or treatment of Anorexia Nervosa.

The blood-brain barrier is bypassed in the present invention by application of at least an effective amount of insulin and/or pharmaceutical composition(s) comprising insulin and/or composition(s) or compound(s) to the upper third of the nasal cavity of the patient, e.g., a mammal. The administered amount of the insulin and/or pharmaceutical composition thereof of the invention migrate from the nasal mucosa through foramina in the cribriform plate along the olfactory neural pathway and an effective amount is delivered directly into the CNS. Further, vasoconstrictors may be applied to the nasal cavity of the patient, either before or during the application of the at least an effective amount of insulin and/or pharmaceutical composition(s) thereof to the upper third of the patient's nasal cavity, to enhance the efficiency of delivery of the an effective amount of insulin to the patient's CNS and minimization of any potential systemic exposure of the administered insulin.

Administration to the nasal cavity employing a neural pathway can thus deliver an effective amount of therapeutic agent(s), e.g., insulin and/or pharmaceutical compositions thereof to the lymphatic system, brain stem, cerebellum, spinal cord, and cortical and subcortical structures of the mammalian patient. The therapeutic agent(s), e.g., insulin and/or pharmaceutical composition(s) thereof of the present invention alone may facilitate this movement into the CNS, i.e., brain, and/or spinal cord. Alternatively, a carrier and/or the delivery-enhancement agent(s) may assist in the transport of the administered insulin and/or pharmaceutical composition of the present invention into and along the neural pathway. Administration of the insulin and/or pharmaceutical composition(s) thereof of the present invention to the upper third of the mammalian patient's nasal cavity thus enables the administered therapeutic agent(s) to bypass the blood-brain barrier through a transport system from the nasal mucosa and/or epithelium to the CNS, i.e., brain and spinal cord where an effective amount of the administered insulin is delivered.

Various embodiments of the invention administer an at least an effective amount of insulin and/or pharmaceutical composition(s) thereof of the present invention to tissue innervated by the olfactory nerves. Such nerve systems can provide a direct connection between the outside environment and the brain, thus providing advantageous delivery of the agent(s) and/or compound(s) to the CNS, including brain, brain stem, and/or spinal cord. The administered insulin and/or pharmaceutical composition(s) thereof of the present invention may be unable to cross or inefficiently cross the blood-brain barrier from the bloodstream into the brain. Alternatively, for those agent(s) and/or composition(s) that may cross the blood-brain barrier, the present invention offers an alternative treatment for those patients having a concurrent system, non-CNS disease or condition that contraindicates systemic administration of the therapeutic agent(s) and/or compositions(s) needed within the CNS to treat a first CNS-related disease, condition or disorder. Thus, the methods of the present invention allow for the delivery of an effective amount of insulin and/or pharmaceutical composition(s) thereof to the target CNS by way of the olfactory nerve rather than through the circulatory system in order to facilitate prevention and/or treatment of Anorexia Nervosa. Thus, this method of administration of at least an effective amount of insulin to the upper third of the nasal cavity and delivery of the effective amount of insulin to the target CNS allows for the efficient and non-invasive delivery of an effective amount of insulin and/or pharmaceutical composition(s) thereof of the present invention to the CNS, brain, or spinal cord without systemic loss or exposure.

Alternative Pathways

Alternative non-systemic pathways to the olfactory nerve pathway discussed above comprise pathways along other nerves that innervate the nasal cavity, e.g., the trigeminal pathway, well known to the skilled artisan.

Delivery-Enhancement Agents

Certain compounds, i.e., delivery-enhancement agents, may be utilized by the present invention to assist the administered at least an effective amount of insulin in delivery of an effective amount of insulin to the central nervous system for prevention and/or treatment of Anorexia Nervosa. A preferred delivery-enhancement agent comprises hyaluronidase which has been observed to very significantly increase delivery of therapeutic agent(s) to the CNS when applied to the upper third of the nasal cavity as either a pretreatment administered in an effective amount prior to the application of the at least an effective amount of insulin according to one embodiment of the present invention, or as a component of the pharmaceutical composition comprising at least an effective amount of insulin, or as a separate compound administered intranasally to the upper third of the nasal cavity substantially simultaneously as the at least an effective amount of insulin and/or pharmaceutical composition. It is believed that the hyaluronidase acts on hyaluronic acid in the extracellular matrix to enhance delivery of the at least an effective amount of insulin and/or pharmaceutical compositions comprising the at least an effective amount of insulin to the CNS.

Alternative delivery-enhancement agents comprise neuregulin, migration-inducing activity and leukemia inhibitory factor. These delivery-enhancement agents, e.g., hyaluronidase, lipophilic agents, neuregulin, migration-inducing activity and leukemia inhibitory factor may be used individually, or in any combination, to enhance delivery of the effective amount of insulin to the CNS according to the present invention. Therefore, at least one delivery-enhancement agent may be used as a pretreatment to transportation of the effective amount of insulin and/or pharmaceutical composition comprising the insulin for treatment of Anorexia Nervosa.

Alternative delivery-enhancement agents that further enhance the mucosal delivery of therapeutic agent(s) such as insulin and/or pharmaceutical composition comprising therapeutic agent(s) such as insulin of the present invention, comprise an enzyme inhibitor, particularly proteases inhibitors as is well known to those in the art. Protease inhibitors may include, but are limited to, antipain, arphamenine A and B, benzamidine HCl, AEBSF, CA-074, calpain inhibitor I and II, calpeptin, pepstatin A, actinonin, amastatin, bestatin, boroleucine, captopril, chloroacetyl-HOLeu-Ala-Gly-NH2, DAPT, diprotin A and B, ebelactone A and B, foroxymithine, leupeptin, pepstatin A, phosphoramidon, aprotinin, puromycin, BBI, soybean trypsin inhibitor, phenylmethylsulfonyl fluoride, E-64, chymostatin, 1,10-phenanthroline, EDTA and EGTA.

Still further alternative delivery-enhancement agents may include, but are not limited to, surfactants, bile salts, dihydrofusidates, bioadhesive agents, phospholipid additives, mixed micelles, liposomes, or carriers, alcohols, enamines, cationic polymers, NO donor compounds, long-chain amphipathic molecules, small hydrophobic penetration enhancers; sodium or a salicylic acid derivatives, glycerol esters of acetoacetic acid, cyclodextrin or beta-cyclodextrin derivatives, medium-chain fatty acids, chelating agents, amino acids or salts thereof, N-acetylamino acids or salts thereof, mucolytic agents, enzymes specifically targeted to a selected membrane component, inhibitors of fatty acid synthesis and inhibitors of cholesterol synthesis. The present invention contemplates using one or more, i.e., at least one, of the above delivery-enhancement agents, either alone or in combination with the at least an effective amount of insulin comprising for delivery to the CNS in an effective amount to treat the patient's Anorexia Nervosa.

Antibiotic Agents

In various embodiments, the present invention may further comprise an effective amount of at least one antibiotic, or alternatively at least one antibiotic(s) pretreatment administered prior to application of the at least an effective amount of insulin and/or pharmaceutical composition to the upper third of the mammalian patient's nasal cavity may be used, or any combination thereof, to protect the patient undergoing treatment from nasal bacteria migrating along the neural pathway followed by the therapeutic agent(s) and/or pharmaceutical composition(s) according to the present invention. Further, the antibiotic(s) may be delivered as a pretreatment, co-treatment and/or post treatment systemically and/or by application to the upper third of the nasal cavity. The utility of such an antibiotic element within the present invention is to reduce the risk that bacteria found in the nasal cavity may enter the nasal tissues at the upper third of the nasal cavity during application of the therapeutic agent(s) and/or pharmaceutical composition, cross the blood-brain barrier and infect other tissues within the CNS. Particular tissues of concern include, but are not limited to, the brain, meninges, blood, spinal cord, and other peripheral tissues. A preferred embodiment is to pretreat and/or simultaneously treat the patient with antibiotic(s) when the delivery-enhancement agent(s), e.g., hyaluronidase, is applied to the upper third of the nasal cavity.

For example, in one study, mupirocin smeared inside the nose cut infection rates in half or better *Staphylococcus aureus* is a widely distributed germ that normally resides in the nostrils of an estimated 25 to 30 percent of all hospitalized patients without causing harm. But this bacterium can contaminate surgical sites, causing severe and often deadly infections, especially in people with weakened immune systems.

Another study found that nasal xylitol, an over the counter remedy sold in health food stores, can reduce nasal bacteria and their ability to hold onto and infect cells in the nasal mucosa. Still other studies have found that defensins, a natural antibiotic found in mucosa in the human, can protect against bacterial infection and enhance immune protective function. Mammalian defensins are small, cationic, antimicrobial peptides encoded by the host that are considered to be important antibiotic-like effectors of innate immunity. By using chemokine receptors on dendritic cells and T cells, defensins might also contribute to the regulation of host adaptive immunity against microbial invasion. Defensins have considerable immunological adjuvant activity and linkage of beta-defensins or selected chemokines to an idiotypic lymphoma antigen has yielded potent antitumor vaccines. The functional overlap between defensins and chemokines is reinforced by reports that some chemokines have antimicrobial activities. Although showing similarity in activity and overall tertiary structure, the evolutionary relationship between defensins and chemokines remains to be determined. (De Yang, et al, Mammalian defensins in immunity: more than just microbicidal. Trends Immunol. 2002 June; 23 (6):291-6 12072367).

Exemplary antibiotics for use in the present invention comprise mupirocin, defensin, gentamycin, geneticin, cefminoxime, penicillin, streptomycin, xylitol, or other antibiotic, either alone or in combination to assist in protecting the patient who is receiving therapeutic agent(s) and/or pharmaceutical composition of the present invention. The use of such antibiotics within nasal treatments is widely reported in the literature as will be readily recognized by the skilled artisan, however no such nasal treatment is reported in conjunction with the intranasal application of therapeutic agent(s) such as insulin and/or pharmaceutical compositions to the upper third of the nasal cavity whereby the blood-brain barrier is bypassed and wherein the subject mammalian patient further comprises a second non-CNS, systemic disease, disorder or condition that contraindicates the systemic administration of the at least an effective amount of insulin and/or pharmaceutical composition comprising at least an effective amount of insulin applied to the upper third of the nasal cavity for direct delivery to the CNS and treatment of Anorexia Nervosa.

Administration of Therapeutic Agent(s) and/or Pharmaceutical Compounds

Administering insulin according to the methods of the invention for treatment of Anorexia Nervosa may include application of at least an effective amount of the therapeutic agent, i.e., insulin alone or formulating the at least an effective amount of insulin with at least an effective amount of one or more of the compounds described supra as pharmaceutical compositions and administering the pharmaceutical compositions to a mammalian subject or host, including a human patient, intranasally to the upper third of the nasal cavity. The therapeutic agent(s) and/other components of the pharmaceutical composition thereof, e.g., vasoconstrictor, delivery-enhancement agent and/or antibiotic may be administered at one of a variety of doses sufficient to provide an effective amount at the desired point of action in the CNS for the administered at least an effective amount of insulin and/or pharmaceutical composition component.

As noted, vasoconstrictor(s), delivery-enhancement agent(s), and/or antibiotic(s) may be delivered as pre-treatment, co-treatment and/or post-treatment with the therapeutic agent(s) and/or pharmaceutical composition, either alone or as a component of the pharmaceutical composition. Delivery of at least an effective amount of insulin in this manner results in delivery of an effective amount of insulin to the target CNS with maximum efficiency in the delivery of insulin, i.e., with minimal to no systemic exposure of insulin.

For application to the upper third of the nasal cavity as suspensions, aerosols, sprays or drops, the at least an effective amount of insulin and/or pharmaceutical composition(s) can be prepared according to techniques well known in the art of pharmaceutical formulation. The compositions can be prepared as suspensions of the agent(s) in solutions which may comprise salts such as saline, components such as phosphate, succinate or citrate buffers to maintain pH, osmoregulatory and osmotic agents such as taurine, and suitable preservatives, absorption promoters to enhance bioavailability, fluorocarbons or other solubilizing or dispersing agents known in the art. The means of applying a pharmaceutical composition intranasally to the upper third of the nasal cavity may be in a variety of forms such as a powder, spray, gel or nose drops.

Other forms of compositions for administration of the at least an effective amount of insulin and/or pharmaceutical compositions or elements thereof include a suspension of a particulate, such as an emulsion, a liposome, or in a sustained-release form to prolong the presence of the pharmaceutically active agent in an individual. The powder or granular forms of the pharmaceutical composition may be combined with a solution and with a diluting, dispersing or surface-active agent. Additional compositions for administration include a bioadhesive to retain the agent at the site of administration at the upper third of the nasal cavity, for example a spray, paint, or swab applied to the mucosa. A bioadhesive can refer to hydrophilic polymers, natural or synthetic, which, by the hydrophilic designation, can be either water soluble or swellable and which are compatible with the pharmaceutical composition. Such adhesives function for adhering the formulations to the mucosal tissues of the upper third of the nasal cavity. Such adhesives can include, but are not limited to, hydroxypropyl cellulose, hydroxypropyl methylcellulose, hydroxy ethylcellulose, ethylcellulose, carboxymethyl cellulose, dextran, gaur gum, polyvinyl pyrrolidone, pectins, starches, gelatin, casein, acrylic acid polymers, polymers of acrylic acid esters, acrylic acid copolymers, vinyl polymers, vinyl copolymers, polymers of vinyl alcohols, alkoxy polymers, polyethylene oxide polymers, polyethers, and combinations thereof. The composition can also be in the form of lyophilized powder, which can be converted into solution, suspension, or emulsion before administration. The pharmaceutical composition is preferably sterilized by membrane filtration and is stored in unit-dose or multi-dose containers such as sealed vials or ampoules.

The pharmaceutical composition may be formulated in a sustained-release form to prolong the presence of the active therapeutic agent(s) in the treated individual. Many methods of preparation of a sustained-release formulation are known in the art and are disclosed in Remington's Pharmaceutical Sciences. Generally, the therapeutic agent(s), pharmaceutical composition and/or components of the pharmaceutical composition, i.e., vasoconstrictor, delivery-enhancement agent and/or antibiotic may be entrapped in semi-permeable matrices of solid hydrophobic polymers. The matrices can be shaped into films or microcapsules. Matrices can include, but are not limited to, polyesters, co-polymers of L-glutamic acid and gamma ethyl-L-glutamate, polylactides, polylactate polyglycolate, hydrogels, non-degradable ethylene-vinyl acetate, degradable lactic acid-glycolic acid copolymers, hyaluronic acid gels, and alginic acid suspensions. Suitable microcapsules can also include hydroxymethylcellulose or gelatin and poly-methyl methacrylate. Microemulsions or colloidal drug delivery systems such as liposomes and albumin microspheres can also be used.

Delivery Systems

The therapeutic agent, i.e., insulin, and/or a pharmaceutical composition comprising at least an effective dose of insulin and/or components of the pharmaceutical composition of the present invention may further be dispensed and applied to the upper third of the nasal cavity as a powdered or liquid nasal spray, suspension, nose drops, a gel, film or ointment, through a tube or catheter, by syringe, by packtail, by pledget (a small flat absorbent pad), by nasal tampon or by submucosal infusion. In some aspects of the present invention, the methods comprise administering to an individual the at least an effective dose of insulin and/or a pharmaceutical composition thereof to the upper third of the nasal cavity by way of a delivery device. Nasal drug delivery can be carried out using devices including, but not limited to, unit dose containers, pump sprays, droppers, squeeze bottles, airless and preservative-free sprays, nebulizers (devices used to change liquid medication to an aerosol particulate form), metered dose inhalers, and pressurized metered dose inhalers. In some aspects, an accurate effective dosage amount is contained within a bioadhesive patch that is placed directly within and on the upper third of a nasal cavity.

At least an effective dose of insulin and/or a pharmaceutical composition comprising at least an effective dose of insulin and/or components of the therapeutic composition of the present invention may be conveniently delivered to the upper third of the nasal cavity in the form of an aerosol spray using a pressurized pack or a nebulizer and a suitable propellant including, but not limited to: dichlorodifluoromethane, trichlorofluoromethane, dichlorotetrafluoroethane, hydrocarbons, compressed air, nitrogen or carbon dioxide. An aerosol system requires the propellant to be inert towards the therapeutic agent(s) and/or pharmaceutical composition as will be readily recognized by the skilled artisan. In the case of a pressurized aerosol, the dosage unit may be controlled by providing a valve to deliver an accurately metered amount.

The means to deliver the at least an effective amount of insulin or pharmaceutical composition comprising the at least an effective amount of insulin and/or components of the pharmaceutical composition of the present invention to the upper third of the nasal cavity as a powder may be in a form such as microspheres delivered by a nasal insufflator device (a device to blow a gas, powder, or vapor into a cavity of the body) or pressurized aerosol canister. The insufflator produces a finely divided cloud of the dry powder or microspheres. The insufflator may be provided with means to ensure administration of a substantially metered amount of the pharmaceutical composition. The powder or microspheres should be administered in a dry, air-dispensable form. The powder or microspheres may be used directly with an insufflator which is provided with a bottle or container for the powder or microspheres. Alternatively the powder or microspheres may be filled into a capsule such as a gelatin capsule, or other single dose device adapted for nasal administration. The insufflator can have means such as a needle to break open the capsule or other device to provide holes through which jets of the powdery composition can be delivered to the upper third of the nasal cavity.

Intermittent and Cyclic Dosing

In various embodiments of the invention, therapeutic agent, i.e., insulin, and/or a pharmaceutical composition comprising at least an effective amount of insulin and/or the components of the pharmaceutical composition may be administered as a single and one-time dose, or alternatively the at least an effective amount of insulin and/or the components of the pharmaceutical composition may be administered more than once and intermittently. By "intermittent administration" is intended administration of at least an effective amount of insulin and/or the components of the pharmaceutical composition, followed by a time period of discontinuance, which is then followed by another administration of the at least effective amount, and so forth. Administration of the at least an effective amount of insulin and/or the components of the pharmaceutical composition may be achieved in a continuous manner, as for example with a sustained-release formulation, or it may be achieved according to a desired daily dosage regimen, as for example with one, two, three, or more administrations per day. By "time period of discontinuance" is intended a discontinuing of the continuous sustained-released or daily administration of the insulin and/or the components of the pharmaceutical composition. The time period of discontinuance may be longer or shorter than the period of continuous sustained-release or daily administration. During the time period of discontinuance, the concentration(s) of insulin and/or the components of the pharmaceutical composition level in the relevant tissue is substantially below the maximum level obtained during the treatment. The preferred length of the discontinuance period depends on the concentration of the effective dose and the form of therapeutic agent(s) and/or the components of the pharmaceutical composition used. The discontinuance period can be at least 2 days, preferably is at least 4 days, more preferably is at least 1 week and generally does not exceed a period of 4 weeks. When a sustained-release formulation is used, the discontinuance period must be extended to account for the greater residence time of the at least one therapeutic agent. Alternatively, the frequency of administration of the effective dose of the sustained-release formulation can be decreased accordingly. An intermittent schedule of administration of insulin and/or the components of the pharmaceutical composition may continue until the desired therapeutic effect, and ultimately treatment of the disease or disorder is achieved.

In yet another embodiment, intermittent administration of the at least an effective amount(s) of insulin and/or the components of the pharmaceutical composition is cyclic. The term "cyclic" is intended herein to refer to intermittent administration accompanied by breaks in the administration, with cycles ranging from about 1 month to about 2, 3, 4, 5, or 6 months. For example, the administration schedule might be intermittent administration of the at least an effective dose of insulin and/or the components of the pharmaceutical composition, wherein a single short-term dose is given once per week for 4 weeks, followed by a break in intermittent administration for a period of 3 months, followed by intermittent administration by administration of a single short-term dose given once per week for 4 weeks, followed by a break in intermittent administration for a period of 3 months, and so forth. As another example, a single short-term dose may be given once per week for 2 weeks, followed by a break in intermittent administration for a period of 1 month, followed by a single short-term dose given once per week for 2 weeks, followed by a break in intermittent administration for a period of 1 month, and so forth. A cyclic intermittent schedule of administration of insulin and/or the components of the pharmaceutical composition to a subject may continue until the desired therapeutic effect, and ultimately treatment of the disorder or disease is achieved.

The invention has been described with reference to various specific and preferred embodiments and techniques. However, it should be understood that many variations and modifications may be made while remaining within the spirit and scope of the invention.

I claim:

1. A method for treating Anorexia Nervosa in a patient that has blood glucose and blood insulin levels within normal limits, comprising:
   administering at least an effective amount of insulin to the upper third of the nasal cavity of the patient;
   enabling at least an effective amount of insulin to directly access the patient's central nervous system by bypassing the blood-brain barrier; and
   treating the patient's Anorexia Nervosa while not altering the patient's systemic non-CNS blood glucose or blood insulin to unsafe levels, outside the normal limits.

2. The method of claim 1, further comprising administering the insulin to a tissue innervated by the olfactory nerve, wherein the administered insulin bypasses the blood-brain barrier to access the patient's central nervous system to treat the Anorexia Nervosa.

3. The method of claim 2, further comprising the administered insulin bypassing the blood-brain barrier by migrating along a neural pathway into the patient's central nervous system to treat the patient's Anorexia Nervosa.

4. The method of claim 1, wherein the administered insulin comprises a non-zinc insulin.

5. The method of claim 1, further comprising pretreating the patient's nasal cavity with an effective amount of at least one vasoconstrictor before administering the insulin to the upper third of the patient's nasal cavity.

6. The method of claim 1, further comprising administering an effective amount of a delivery enhancement agent to the upper third of the patient's nasal cavity.

7. The method of claim 1, further comprising:
   providing a pharmaceutical composition comprising the at least an effective amount of insulin and an effective amount of at least one of the group consisting of a vasoconstrictor, and a delivery enhancement agent;
   administering an effective amount of the pharmaceutical composition to the upper third of the mammal's nasal cavity, thereby enabling the effective amount of the pharmaceutical composition to bypass the blood-brain barrier and directly delivering the effective amount of the pharmaceutical composition directly to the patient's central nervous system to prevent or treat the patient's Anorexia Nervosa.

8. The method of claim 7, wherein the delivery-enhancement agent further comprises one of the group consisting of hyaluronidase, migration-inducing activity and neuregulin.

9. The method of claim 1, wherein the at least an effective amount of insulin is in the range of $1\times10^{-7}$ to 0.1 mg/kg.

10. The method of claim 9, wherein a dosage range for the at least an effective amount of insulin is in the range of $1\times10^{-4}$ to 0.1 mg/kg.

11. The method of claim 1, wherein the concentration of insulin in the brain of the patient after a single dose is in the range of $1\times10^{-3}$ to $1\times10^{-9}$ molar.

12. A method of treating a patient with Anorexia Nervosa having blood glucose and/or blood insulin levels that are not within normal limits, comprising:
   administering at least an effective amount of insulin to the upper third of the nasal cavity of the patient;

enabling at least an effective amount of insulin to directly access the patient's central nervous system by bypassing the blood-brain barrier; and safely treating the patient's Anorexia Nervosa without significantly affecting the patient's systemic non-CNS blood glucose or insulin levels.

13. The method of claim 12, further comprising pretreating the patient's nasal cavity with an effective amount of at least one vasoconstrictor before administering the insulin to the upper third of the patient's nasal cavity.

14. The method of claim 12, further comprising administering an effective amount of a delivery enhancement agent to the upper third of the patient's nasal cavity.

15. The method of claim 12, further comprising:
providing a pharmaceutical composition comprising the at least an effective amount of insulin and an effective amount of at least one of the group consisting of a vasoconstrictor, and a delivery enhancement agent;
administering an effective amount of the pharmaceutical composition to the upper third of the mammal's nasal cavity, thereby enabling the effective amount of the pharmaceutical composition to bypass the blood-brain barrier; and
directly delivering the effective amount of the pharmaceutical composition directly to the patient's central nervous system to prevent or treat the patient's Anorexia Nervosa.

16. The method of claim 15, wherein the delivery-enhancement agent further comprises one of the group consisting of hyaluronidase, migration-inducing activity and neuregulin.

17. The method of claim 12, wherein the at least an effective amount of insulin is in the range of $1 \times 10^{-7}$ to 0.1 mg/kg.

18. The method of claim 17, wherein a dosage range for the at least an effective amount of insulin is in the range of $1 \times 10^{-4}$ to 0.1 mg/kg.

19. The method of claim 12, wherein the concentration of insulin in the brain of the patient after a single dose in the range of $1 \times 10^{-13}$ to $1 \times 10^{-9}$ molar.

* * * * *